US010163228B2

(12) United States Patent
Kim et al.

(10) Patent No.: US 10,163,228 B2
(45) Date of Patent: Dec. 25, 2018

(54) MEDICAL IMAGING APPARATUS AND METHOD OF OPERATING SAME

(71) Applicant: SAMSUNG MEDISON CO., LTD., Hongcheon-gun (KR)

(72) Inventors: Won-sik Kim, Gunpo-si (KR); Moon-ho Park, Hwaseong-si (KR); Yeong-kyeong Seong, Suwon-si (KR); Boo-kyung Han, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 0 days.

(21) Appl. No.: 15/174,127

(22) Filed: Jun. 6, 2016

(65) Prior Publication Data

US 2017/0148190 A1 May 25, 2017

(30) Foreign Application Priority Data

Nov. 25, 2015 (KR) .................. 10-2015-0165572

(51) Int. Cl.
*G06T 11/00* (2006.01)
*G06T 11/20* (2006.01)
(Continued)

(52) U.S. Cl.
CPC ............ *G06T 11/001* (2013.01); *A61B 8/085* (2013.01); *A61B 8/145* (2013.01); *A61B 8/463* (2013.01); *A61B 8/483* (2013.01); *A61B 8/5223* (2013.01); *A61B 8/5292* (2013.01); *G06T 11/206* (2013.01); *A61B 5/055* (2013.01); *A61B 6/03* (2013.01); *A61B 6/5294* (2013.01); *A61B 2576/00* (2013.01); *G06T 2200/24* (2013.01);
(Continued)

(58) Field of Classification Search
None
See application file for complete search history.

(56) References Cited

U.S. PATENT DOCUMENTS 7,631,309 B2 * 12/2009 Wilt ...................... G06F 9/3851
710/52
7,640,051 B2 12/2009 Krishnan et al.
(Continued)

FOREIGN PATENT DOCUMENTS

EP 2764821 A1 8/2014
JP 5364238 A 12/2013

OTHER PUBLICATIONS

Jonathan Denning (MeshFlow: Interactive Visualization of Mesh Construction Sequences, https://youtube.com/watch?v=oTH7zwS_Wto, Jun. 13, 2011.*

(Continued)

*Primary Examiner* — Nicholas R Wilson
(74) *Attorney, Agent, or Firm* — Sughrue Mion, PLLC

(57) ABSTRACT

Provided is a medical imaging apparatus including: an image processor configured to extract properties that an object has with respect to at least one feature, based on a plurality of medical images of the object; and a controller configured to control a display to display a first medical image from among the plurality of medical images and the extracted properties and display a first property shown in the first medical image from among the properties and a second property not shown in the first medical image in such a manner that the first property and the second property are distinguished from each other.

14 Claims, 14 Drawing Sheets

(51) Int. Cl.
*A61B 8/08* (2006.01)
*A61B 8/14* (2006.01)
*A61B 8/00* (2006.01)
*A61B 6/03* (2006.01)
*A61B 6/00* (2006.01)
*A61B 5/055* (2006.01)

(52) U.S. Cl.
CPC ............... *G06T 2207/10088* (2013.01); *G06T 2207/10132* (2013.01); *G06T 2207/30096* (2013.01); *G06T 2210/41* (2013.01)

(56) References Cited

U.S. PATENT DOCUMENTS

| | | | |
|---|---|---|---|
| 8,452,613 | B2 | 5/2013 | Meinel et al. |
| 8,799,013 | B2 | 8/2014 | Gustafson |
| 2003/0007598 | A1* | 1/2003 | Wang ............... A61B 6/463 378/37 |
| 2003/0212327 | A1* | 11/2003 | Wang ............... A61B 6/463 600/437 |
| 2009/0009512 | A1 | 1/2009 | Dolimier et al. |
| 2010/0141654 | A1 | 6/2010 | Neemuchwala et al. |
| 2011/0137132 | A1* | 6/2011 | Gustafson ............ A61B 5/4312 600/300 |
| 2011/0295118 | A1 | 12/2011 | Okamura |

OTHER PUBLICATIONS

Bocchi et al., "Semiautomated Breast Cancer Classification From Ultrasound Video", 2012, 4 pages total, IEEE, Florence, Italy.

Kanne et al. "Enhancement of CADx Accuracy by Using Multiple Slices from Various Views in 3D Liver Ultrasound", 99th Scientific Assembly and Annual Meeting, Dec. 1-6, 2013, 78 pages total, RSNA 2013, Chicago, USA (Only Abstract being submitted).

Communication dated May 2, 2017, issued by the European Patent Office in counterpart European Application No. 16183811.5.

* cited by examiner

FIG. 9A
FIG. 9B
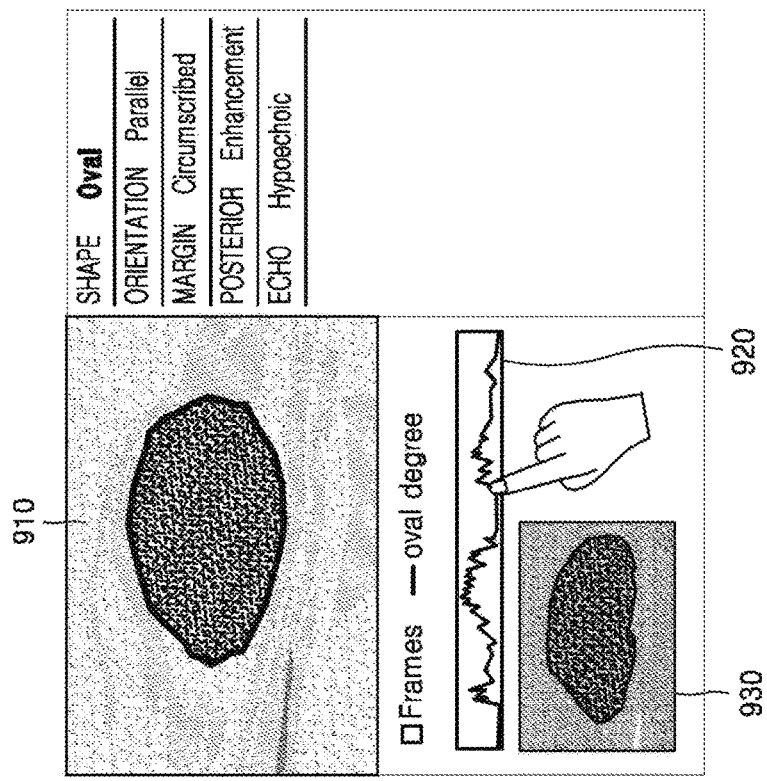
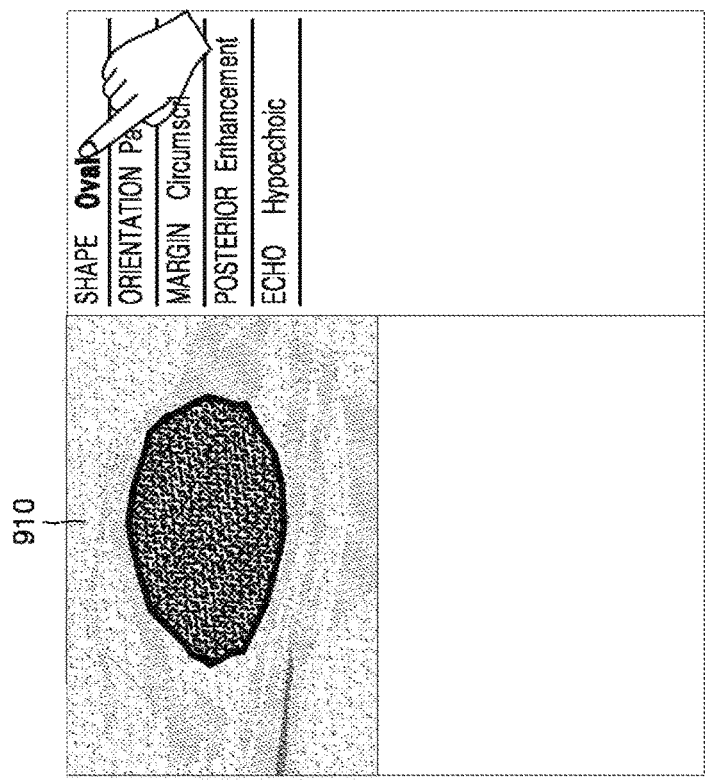

MEDICAL IMAGING APPARATUS AND METHOD OF OPERATING SAME

CROSS-REFERENCE TO RELATED APPLICATION

This application claims the benefit of Korean Patent Application No. 10-2015-0165572, filed on Nov. 25, 2015, in the Korean Intellectual Property Office, the disclosure of which is incorporated herein in its entirety by reference.

BACKGROUND

1. Field

The present disclosure relates to medical imaging apparatuses and methods of operating the same, and more particularly, to medical imaging apparatuses and operation methods for extracting properties of a lesion observed in an object by using a plurality of medical images showing the object and displaying the extracted properties.

2. Description of the Related Art

Recently, in the medical field, various types of medical imaging apparatuses for imaging information about biological tissue of the human body and obtaining resultant images of the biological tissue have been widely used for early diagnosis or surgical treatment of diseases. Representative examples of medical imaging apparatuses may include an ultrasound diagnosis apparatus, a computed tomography (CT) apparatus, and a magnetic resonance imaging (MRI) apparatus.

Ultrasound diagnosis apparatuses transmit ultrasound signals generated by transducers of a probe to an object and receive echo signals reflected from the object, thereby obtaining at least one image of an internal part of the object. In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound imaging apparatuses are widely used together with other image diagnosis apparatuses.

In addition, an ultrasound diagnosis apparatus may support a brightness (B) mode, a Doppler mode, an elastic mode, and the like. In the B mode, a reflection coefficient of an ultrasound signal is visualized as a two-dimensional (2D) image. In the Doppler mode, a velocity of a moving object (in particular, blood flow) is shown as an image by using the Doppler effect. In the elastic mode, a difference between responses when compression is or not applied to an object is visualized as an image.

SUMMARY

Provided are medical imaging apparatuses and operation methods for extracting properties of a lesion observed in an object based on a plurality of medical images and displaying the extracted properties in such a manner as to distinguish properties shown in a medical image displayed on a display and those not shown therein.

Additional aspects will be set forth in part in the description which follows and, in part, will be apparent from the description, or may be learned by practice of the presented embodiments.

According to an aspect of an embodiment, a medical imaging apparatus includes: an image processor configured to extract properties that an object has with respect to at least one feature, based on a plurality of medical images of the object; and a controller configured to control a display to display a first medical image from among the plurality of medical images and the extracted properties and display a first property shown in the first medical image from among the properties and a second property not shown in the first medical image in such a manner that the first property and the second property are distinguished from each other.

The medical imaging apparatus may further include a data acquisition unit configured to acquire ultrasound data with respect to the object, and the image processor may generate a plurality of ultrasound images based on the ultrasound data, and extract the properties that the object has with respect to the at least one feature, based on the plurality of ultrasound images.

The at least one feature may include at least one of a shape, an orientation, a margin, a posterior, and an echo.

The controller may control the display to display the first property in a first color and display the second property in a second color that is different from the first color.

The controller may control the display to display the first property in a first region and display the second property in a second region that is distinguished from the first region.

The medical imaging apparatus may further include an input device configured to receive an input for selecting the second property, and the controller may control the display to display a second medical image showing the selected second property from among the plurality of medical images.

The medical imaging apparatus may further include an input device configured to receive an input for selecting the second property, and the controller may control the display to display a frame bar including lines respectively corresponding to the plurality of medical images and to display a line corresponding to a medical image showing the selected second property from among the lines and a line corresponding to a medical image not showing the second property in such a manner that the lines are distinguished from each other.

The input device may receive an input for selecting one of the lines in the frame bar, and the controller may control the display to display a medical image corresponding to the selected line.

The medical imaging apparatus may further include an input device configured to receive an input for selecting the second property, and the controller may control the display to display a graph obtained by quantifying a degree to which the second property is shown in each of the plurality of medical images.

The input device may receive an input for selecting a point on the graph, and the controller may control the display to display a medical image corresponding to the selected point.

According to an aspect of another embodiment, a method of operating a medical imaging apparatus includes: extracting properties that an object has with respect to at least one feature based on a plurality of medical images of the object; and displaying a first medical image from among the plurality of medical images and the extracted properties and displaying a first property shown in the first medical image from among the properties and a second property not shown in the first medical image in such a manner that the first property and the second property are distinguished from each other.

The method may further include acquiring ultrasound data with respect to the object, and the extracting of the properties may include: generating a plurality of ultrasound images based on the ultrasound data; and extracting the properties that the object has with respect to the at least one feature based on the plurality of ultrasound images.

The displaying of the first property and the second property in such a manner that the first property and the second property are distinguished from each other may include displaying the first property in a first color and displaying the second property in a second color that is different from the first color.

The displaying of the first property and the second property in such a manner that the first property and the second property are distinguished from each other may include displaying the first property in a first region and displaying the second property in a second region that is distinguished from the first region.

The method may further include: receiving an input for selecting the second property; and displaying a second medical image showing the selected second property from among the plurality of medical images.

The method may further include: receiving an input for selecting the second property; and displaying a frame bar including lines respectively corresponding to the plurality of medical images and displaying a line corresponding to a medical image showing the selected second property from among the lines and a line corresponding to a medical image not showing the second property in such a manner that the lines are distinguished from each other.

The method may further include receiving an input for selecting one of the lines in the frame bar and displaying a medical image corresponding to the selected line.

The method may further include receiving an input for selecting the second property and displaying a graph obtained by quantifying a degree to which the second property is shown in each of the plurality of medical images.

The method may further include receiving an input for selecting a point on the graph and displaying a medical image corresponding to the selected point.

According to an embodiment, by extracting properties of an object based on a plurality of medical images, it is possible to accurately extract the properties of the object.

According to an embodiment, it is possible to reliably provide a user with the extracted properties by displaying the extracted properties in such a manner as to distinguish properties shown in a medical image displayed on a display and those not shown therein.

According to an embodiment, user convenience may be increased by providing an interface configured to efficiently search for a medical image reflecting properties not shown in a medical image displayed on a display from among extracted properties.

BRIEF DESCRIPTION OF THE DRAWINGS

These and/or other aspects will become apparent and more readily appreciated from the following description of the embodiments, taken in conjunction with the accompanying drawings in which reference numerals denote structural elements and in which:

FIGS. 6A through 10B are diagrams for explaining a method, performed by a medical imaging apparatus, of displaying a medical image corresponding to a selected property, according to embodiments;

DETAILED DESCRIPTION

Figure 1:
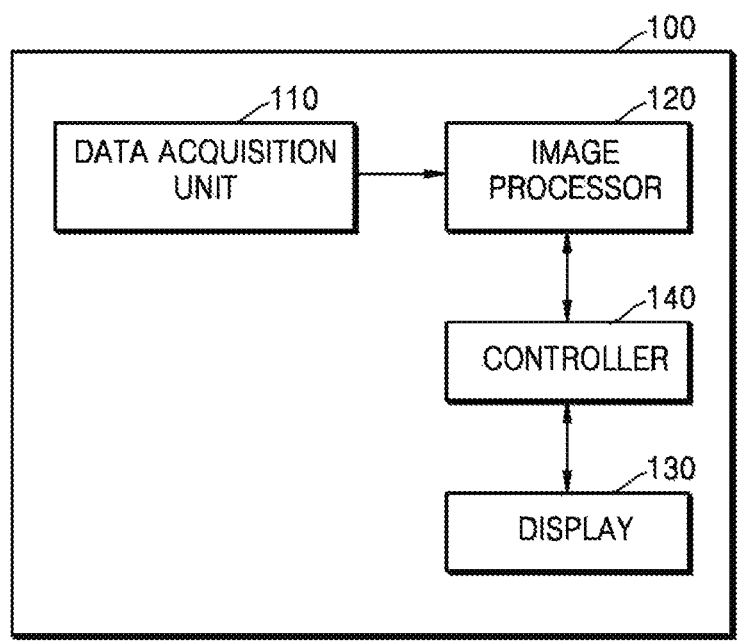
FIG. 1 is a block diagram of a configuration of a medical imaging apparatus according to an embodiment.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used in the specification should be understood not as simple names but based on the meaning of the terms and the overall description of the invention. Expressions such as "at least one of," when preceding a list of elements, modify the entire list of elements and do not modify the individual elements of the list.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, an "image" may refer to multi-dimensional data composed of discrete image elements. Examples of an image may include medical images, i.e., an ultrasound image, a computed tomography (CT) image, a magnetic resonance (MR) image respectively obtained by an ultrasound apparatus, a CT apparatus, and an MR imaging (MRI) apparatus, but are not limited thereto.

Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body. Furthermore, the object may be a lesion occurring in an organ, a blood vessel, etc.

An ultrasound image may be an image obtained by transmitting ultrasound signals generated by transducers of a probe to an object and receiving information about echo signals reflected from the object. Furthermore, an ultrasound image may take different forms. For example, the ultrasound image may be at least one of an amplitude (A) mode image, a brightness (B) mode image, a color (C) mode image, and a Doppler (D) mode image. In addition, according to an embodiment, an ultrasound image may be a two-dimensional (2D) or three-dimensional (3D) image.

A "CT image" may mean an image generated by synthesizing a plurality of X-ray images that are obtained by photographing an object while a CT imaging apparatus rotates around at least one axis with respect to the object.

An "MR image" may mean an image of an object obtained using the principles of nuclear magnetic resonance (NMR).

Throughout the specification, a "user" may be, but is not limited to, a medical expert, for example, a medical doctor, a nurse, a medical laboratory technologist, or a medical imaging expert, or a technician who repairs medical apparatuses.

Embodiments will now be described more fully hereinafter with reference to the accompanying drawings so that they may be easily implemented by one of ordinary skill in the art. However, the present embodiments may have different forms and should not be construed as being limited to the descriptions set forth herein.

FIG. 1 is a block diagram of a configuration of a medical imaging apparatus 100 according to an embodiment. Referring to FIG. 1, the medical imaging apparatus 100 according to the present embodiment may include a data acquisition unit 110, an image processor 120, a controller 140, and a display 130.

According to an embodiment, the data acquisition unit 110 may acquire medical image data with respect to an object. In this case, the medical image data may include ultrasound data, CT data, and MR data, and is not limited thereto.

The data acquisition unit 110 may acquire ultrasound data with respect to an object. For example, the data acquisition unit 110 may transmit ultrasound signals to the object and receive echo signals reflected by the object. The data acquisition unit 110 may generate ultrasound data with respect to the object by processing the received echo signals. Furthermore, the data acquisition unit 110 may transmit a radio frequency (RF) signal to an object and receive an MR signal emitted from the object. The data acquisition unit 110 may generate MR data with respect to the object by processing the received MR signal. Furthermore, the data acquisition unit 110 may transmit an X-ray to an object and detect the X-ray that is transmitted through the object. The data acquisition unit 110 may generate CT data with respect to the object by processing a signal corresponding to the detected X-ray.

However, the data acquisition unit 110 may receive medical image data generated by an external ultrasound diagnosis apparatus, an MR apparatus, a CT apparatus, etc., without directly generating medical image data by receiving an ultrasound signal, an MR signal, an X-ray signal, etc.

According to an embodiment, the medical image data may be 2D data or 3D volume data. 2D data may data representing a cross-section of an object. Volume data means data obtained by stacking pieces of data representing cross-sections of the object and reconstructing the stacked pieces of data into a 3D format.

According to an embodiment, the image processor 120 may generate a plurality of medical images based on medical image data. For example, if ultrasound data is acquired, the image processor 120 may generate an ultrasound image based on the ultrasound data. If MR data is acquired, the image processor 120 may generate an MR image based on the MR data. Furthermore, if CT data is acquired, the image processor 120 may generate a CT image based on the CT data. According to an embodiment, the plurality of medical images may be medical images respectively corresponding to various cross-sections of the object.

For example, if a user input (e.g., a freeze button input) is received during scanning of an object, the image processor 120 may generate an ultrasound image based on ultrasound data acquired at a time point when the user input is received. In this case, if many user inputs are received, the image processor 120 may generate ultrasound images respectively corresponding to time points when the user inputs are received. Furthermore, the image processor 120 may generate a plurality of frame images with respect to the object. In addition, the image processor 120 may generate a plurality of 2D ultrasound images by using 3D volume data with respect to the object, as will be described in detail with reference to FIG. 3. However, methods of generating a plurality of medical images are not limited to the above-described examples, and the plurality of medical images may be generated using various other methods.

In addition, according to an embodiment, the medical imaging apparatus 100 may not directly generate medical images but receive a plurality of generated medical images from an external device.

The image processor 120 may extract properties that the object has with respect to at least one feature, based on the generated plurality of medical images. In this case, the at least one feature may include at least one of a shape, an orientation, a margin, a posterior, and an echo.

Furthermore, the image processor 120 may extract, based on the plurality of medical images, a shape property, an orientation property, a margin property, a posterior property, an echo property of the object, etc.

For example, the image processor may extract properties of the object based on each of the plurality of medical images. According to an embodiment, the image processor 120 may detect an edge of the object based on values of pixels in a medical image. After detecting the edge of the object, the image processor 120 may extract a shape and an orientation of the object based on the detected edge of the object. Furthermore, the image processor may extract brightness of the object based on values of pixels within the object. In this case, reference values or data that are used to determine properties of the object may be prestored in the medical imaging apparatus 100. However, the above methods of extracting properties are merely examples and thus are not limited thereto. Properties of an object may be extracted from a plurality of medical images by using various property extraction methods that are already known in the art.

In this case, properties that occur most frequently among properties extracted from each of the plurality of medical images may be determined as properties of the object. For example, a shape of the object may be shown as being oval or round in the plurality of medical images. If the number of medical images showing a shape of the object as being oval is greater than the number of medical images showing a shape of the object as being round, the shape of the object may be determined to be oval.

The display 130 displays and outputs at least one of the generated plurality of medical images. The display 130 may display and output not only medical images but also various pieces of information processed by the medical imaging apparatus 100 onto a screen via a graphical user interface (GUI). In addition, the medical imaging apparatus 100 may include two or more displays 130 according to embodiments.

According to an embodiment, the controller 140 may control an operation of the display 130. The controller 140 may control the display 130 to display a first medical image from among a plurality of medical images. In this case, the first medical image may be a representative image that best represents extracted properties of the object from among the plurality of medical images. For example, the first medical image may be an image showing a greatest number of types of properties from among the plurality of medical images. Alternatively, the first medical image may be an image selected by the user.

Furthermore, the controller 140 may control the display 130 to display at least one of properties of an object extracted by the image processor 120. The controller 140 may control the display 130 to display a first property shown in a first medical image from among the extracted properties and a second property not shown therein in such a manner that they may be distinguished from each other.

For example, the display 130 may display the first property in a first color and the second property in a second color that is different from the first color. Furthermore, the display 130 may display the first property in a first region and the second property in a second region distinguished from the first region.

According to an embodiment, when the second property is selected, the controller 140 may control the display 130 to display a second medical image showing the selected second property.

Furthermore, the controller 140 may control the display 130 to display a frame bar including lines respectively corresponding to a plurality of medical images. When the second property is selected, the controller 140 may also control the display 130 to display a line corresponding to a medical image showing the selected second property and a line corresponding to a medical image not showing the second property in such a manner that the lines may be distinguished from each other. When one of the lines in the frame bar is selected, the display 130 may display a medical image corresponding to the selected line.

Furthermore, when the second property is selected, the controller 140 may control the display 130 to display a graph obtained by quantifying the degree to which the second property is shown in each of the plurality of medical images. When a point on the graph is selected, the display 130 may display a medical image corresponding to the selected point.

Figure 2:
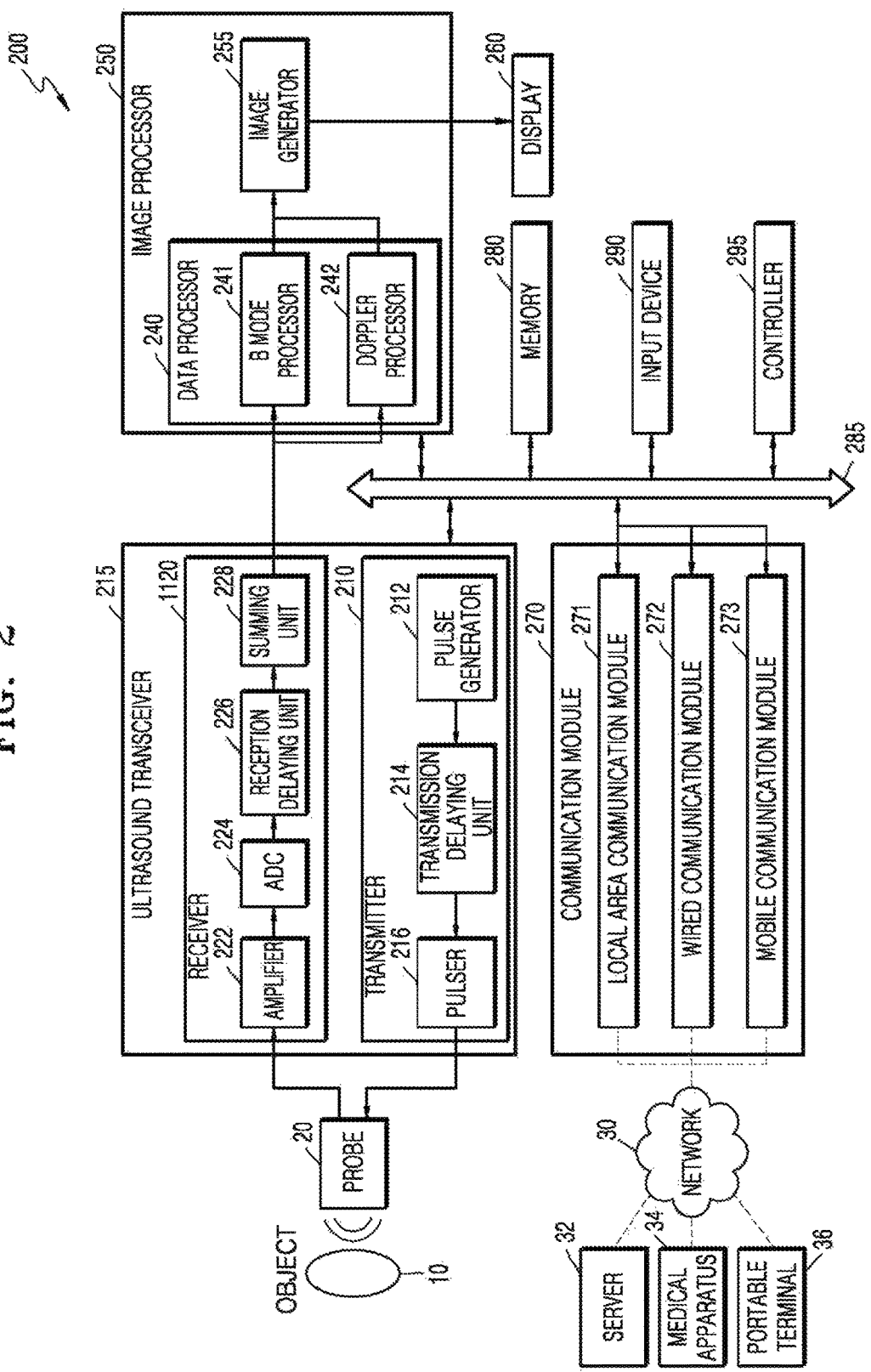
FIG. 2 is a block diagram of a configuration of a medical imaging apparatus according to an embodiment.

FIG. 2 is a block diagram of a configuration of a medical imaging apparatus according to an embodiment.

Referring to FIG. 2, the medical imaging apparatus according to the present embodiment may be an ultrasound diagnosis apparatus 200. The ultrasound diagnosis apparatus 200 may include a probe 20, an ultrasound transceiver 215, an image processor 250, a display 260, a communication module 270, a memory 280, an input device 290, and a controller 295, which may be connected to one another via a bus 285.

The data acquisition unit 110, the image processor 120, the controller 140, and the display 130 described with reference to FIG. 1 may respectively correspond to the ultrasound transceiver 215, the image processor 250, the controller 295, and the display 260 described with reference to FIG. 2. Thus, since descriptions of the data acquisition unit 110, the image processor 120, and the display 130 of FIG. 1 respectively apply to the ultrasound transceiver 215, the image processor 250, and the display 260 of FIG. 2, descriptions already provided with respect to FIG. 2 will be omitted here.

In some embodiments, the ultrasound diagnosis apparatus 200 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 215 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 200 by wire or wirelessly, and according to embodiments, the ultrasound diagnosis apparatus 200 may include a plurality of probes 20.

A transmitter 210 supplies a driving signal to the probe 20. The transmitter 110 includes a pulse generator 212, a transmission delaying unit 214, and a pulser 216. The pulse generator 212 generates pulses for forming transmission ultrasound waves based on a predetermined pulse repetition frequency (PRF), and the transmission delaying unit 214 delays the pulses by delay times necessary for determining transmission directionality. The pulses which have been delayed correspond to a plurality of piezoelectric vibrators included in the probe 20, respectively. The pulser 216 applies a driving signal (or a driving pulse) to the probe 20 based on timing corresponding to each of the pulses which have been delayed.

A receiver 220 generates ultrasound data by processing echo signals received from the probe 20. The receiver 120 may include an amplifier 222, an analog-to-digital converter (ADC) 224, a reception delaying unit 226, and a summing unit 228. The amplifier 222 amplifies echo signals in each channel, and the ADC 224 performs analog-to-digital conversion with respect to the amplified echo signals. The reception delaying unit 226 delays digital echo signals output by the ADC 124 by delay times necessary for determining reception directionality, and the summing unit 228 generates ultrasound data by summing the echo signals processed by the reception delaying unit 226. In some embodiments, the receiver 220 may not include the amplifier 222. In other words, if the sensitivity of the probe 20 or the capability of the ADC 224 to process bits is enhanced, the amplifier 222 may be omitted.

The image processor 250 generates an ultrasound image by scan-converting ultrasound data generated by the ultrasound transceiver 215 and displays the ultrasound image.

An image generator 120 extracts B mode components from ultrasound data and processes the B mode components. The image generator 120 may generate an ultrasound image indicating signal intensities as brightness based on the extracted B mode components 141.

The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color flow image), a tissue Doppler image showing a movement of tissue, or a spectral Doppler image showing a moving speed of an object as a waveform.

A B mode processor 241 extracts B mode components from ultrasound data and processes the B mode components. An image generator 255 may generate an ultrasound image indicating signal intensities as brightness based on the extracted B mode components 241.

Similarly, a Doppler processor 242 may extract Doppler components from ultrasound data, and the image generator 255 may generate a Doppler image indicating a movement of an object as colors or waveforms based on the extracted Doppler components.

According to an embodiment, the image generator 255 may generate a three-dimensional (3D) ultrasound image via volume-rendering with respect to volume data and may also generate an elasticity image by imaging deformation of the object 10 due to pressure.

Furthermore, the image generator 255 may display various pieces of additional information in an ultrasound image by using text and graphics. In addition, the generated ultrasound image may be stored in the memory 280.

The display 260 may include at least one of a liquid crystal display (LCD), a thin film transistor-LCD (TFT-LCD), an organic light-emitting diode (OLED) display, a flexible display, a 3D display, and an electrophoretic display.

Furthermore, when the display 260 and a user interface form a layer structure to form a touch screen, the display 260 may be used not only as an output device but also as an input device via which a user inputs information via a touch.

The touch screen may be configured to detect a position of a touch input, a touched area, and pressure of a touch. The touch screen may also be configured to detect both a real touch and a proximity touch.

The communication module 270 is connected to a network 30 by wire or wirelessly to communicate with an external device or a server. The communication module 270 may exchange data with a hospital server or another medical apparatus in a hospital, which is connected thereto via a PACS. Furthermore, the communication module 170 may perform data communication according to the digital imaging and communications in medicine (DICOM) standard.

The communication module 270 may transmit or receive data related to diagnosis of an object, e.g., an ultrasound image, ultrasound data, and Doppler data of the object, via the network 30 and may also transmit or receive medical images captured by another medical apparatus, e.g., a computed tomography (CT) apparatus, a magnetic resonance imaging (MRI) apparatus, or an X-ray apparatus. Furthermore, the communication module 270 may receive information about a diagnosis history or medical treatment schedule of a patient from a server and utilizes the received information to diagnose the patient. Furthermore, the communication module 270 may perform data communication not only with a server or a medical apparatus in a hospital, but also with a portable terminal of a medical doctor or patient.

The communication module 270 is connected to the network 30 by wire or wirelessly to exchange data with a server 32, a medical apparatus 34, or a portable terminal 36. The communication module 270 may include one or more components for communication with external devices. For example, the communication module 1300 may include a local area communication module 271, a wired communication module 272, and a mobile communication module 273.

The local area communication module 271 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 272 refers to a module for communication using electric signals or optical signals. Examples of wired communication techniques according to an embodiment may include communication via a twisted pair cable, a coaxial cable, an optical fiber cable, and an Ethernet cable.

The mobile communication module 273 transmits or receives wireless signals to or from at least one selected from a base station, an external terminal, and a server on a mobile communication network. The wireless signals may be voice call signals, video call signals, or various types of data for transmission and reception of text/multimedia messages.

The memory 280 stores various data processed by the ultrasound diagnosis apparatus 200. For example, the memory 180 may store medical data related to diagnosis of an object, such as ultrasound data and an ultrasound image that are input or output, and may also store algorithms or programs which are to be executed in the ultrasound diagnosis apparatus 200.

The memory 280 may be any of various storage media, e.g., a flash memory, a hard disk drive, EEPROM, etc. Furthermore, the ultrasound diagnosis apparatus 100 may utilize web storage or a cloud server that performs the storage function of the memory 280 online.

The input device 290 refers to a means via which a user inputs data for controlling the ultrasound diagnosis apparatus 50. The input device 290 may include hardware components, such as a keypad, a mouse, a touch pad, a track ball, and a jog switch, but is not limited thereto. Furthermore, the input device 290 may include a fingerprint recognition sensor to detect a user's fingerprint. The input device 290 may further include any of various other components including an electrocardiogram (ECG) measuring module, a respiration measuring module, a voice recognition sensor, a gesture recognition sensor, an iris recognition sensor, a depth sensor, a distance sensor, etc. In particular, the input device 290 may also include a touch screen in which a touch pad forms a layer structure with the display 260.

In this case, according to an embodiment, the ultrasound diagnosis apparatus 200 may display an ultrasound image in a predetermined mode and a control panel for the ultrasound image on a touch screen. The ultrasound diagnosis apparatus 200 may also detect a user's touch gesture performed on an ultrasound image via the touch screen.

According to an embodiment, the ultrasound diagnosis apparatus 200 may include some buttons that are frequently used by a user among buttons that are included in a control panel of a general ultrasound apparatus, and provide the remaining buttons in the form of a GUI via a touch screen.

The controller 295 may control all operations of the ultrasound diagnosis apparatus 200. In other words, the controller 295 may control operations among the probe 20, the ultrasound transceiver 200, the image processor 250, the communication module 270, the memory 280, and the input device 290 shown in FIG. 2.

All or some of the probe 20, the ultrasound transceiver 215, the image processor 250, the display 240, the communication module 270, the memory 280, the input device 290, and the controller 295 may be implemented as software modules. Furthermore, at least one selected from the ultrasound transceiver 215, the image processor 250, and the communication module 270 may be included in the controller 295. However, embodiments of the prevent inventive concept are not limited thereto.

Figure 3:
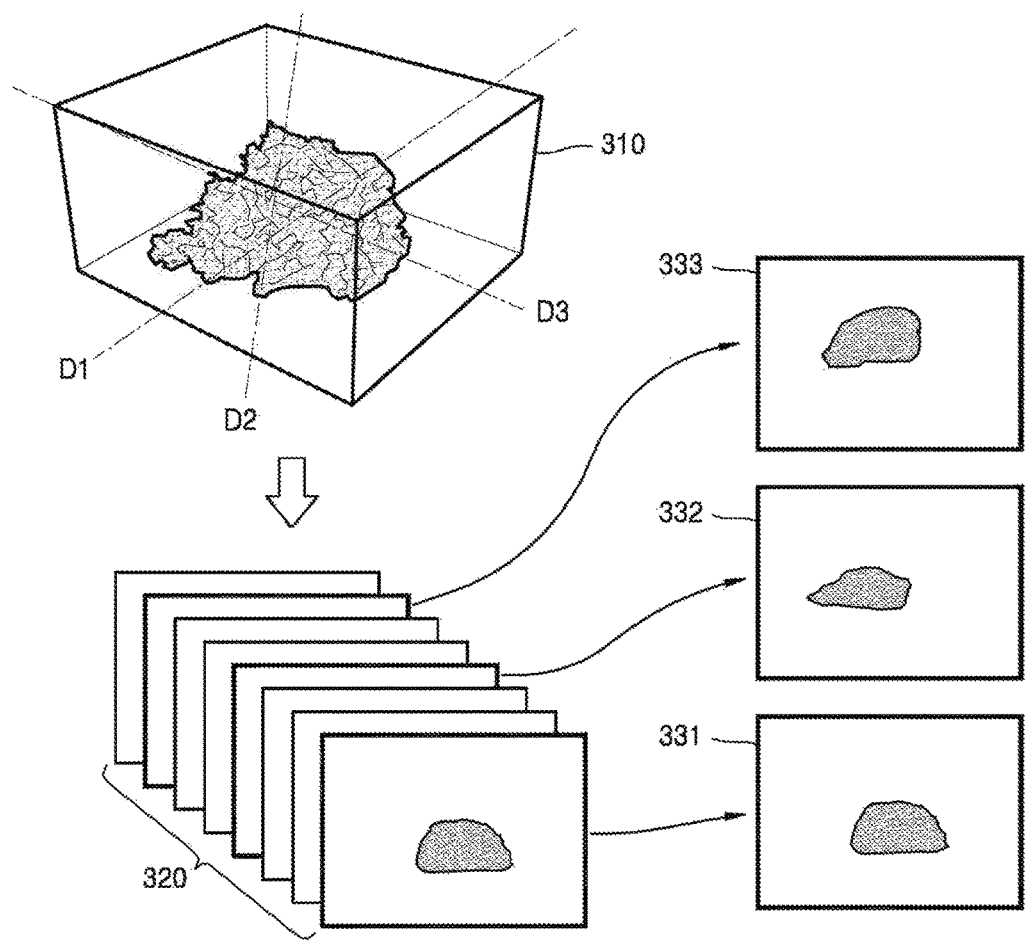
FIG. 3 illustrates a plurality of medical images according to an embodiment.

FIG. 3 illustrates a plurality of medical images according to an embodiment.

Referring to FIG. 3, the medical imaging apparatus 100 of FIG. 1 may acquire 3D volume data 310 with respect to an object.

The medical imaging apparatus 100 may transmit ultrasound signals to the object, receive echo signals reflected by the object, and generate ultrasound data with respect to the object by processing the received echo signals. In this case, the medical imaging apparatus 100 may use a phased probe, a linear probe, and a convex probe to acquire the 3D volume data 310. The 3D volume data 310 means data obtained by stacking pieces of 2D data with respect to the object (pieces of data corresponding to ultrasound cross-sectional images) and reconstructing the stacked pieces of data into a 3D format.

According to an embodiment, the medical imaging apparatus 100 may generate 2D ultrasound images 320 in various directions based on the 3D volume data 310. Furthermore, the medical imaging apparatus 100 may extract properties that the object has with respect to at least one feature, from the generated plurality of 2D ultrasound images 320. In this case, some of the properties extracted from the plurality of 2D ultrasound images 320 may be shown in some of the plurality of 2D ultrasound images 320. For example, if the properties of the object extracted from the plurality of 2D ultrasound images 320 include first through third properties, the first property may be shown only in a first image 331 that is a cross-sectional image obtained from a first direction D1, the second property may be shown only in a second image 332 that is a cross-sectional image obtained from a second direction D2, and the third property may be shown only in a third image 333 that is a cross-sectional image obtained from a third direction D3.

Thus, extracting properties of an object based on a single medical image may degrade the accuracy of the extracted properties since all properties of the object are not included in the single medical image.

According to an embodiment, the medical imaging apparatus 100 may extract properties of the object with respect to at least one feature based on a plurality of medical images of the object, thereby providing increased accuracy in the extracting of properties. Furthermore, the medical imaging apparatus 100 may display at least one of the plurality of medical images and extracted properties. If some of the extracted properties are not shown in a medical image displayed on the display 130, the extracted properties do not match properties shown in the medical image. Thus, a user may not be reliably provided with extracted properties. Thus, according to an embodiment, the medical imaging apparatus 100 may display the extracted properties in such a manner as to distinguish properties shown in a medical image displayed on the display 130 from properties not shown therein, thereby providing a user with reliability of the extracted properties, as will be described in detail below.

Figure 4:
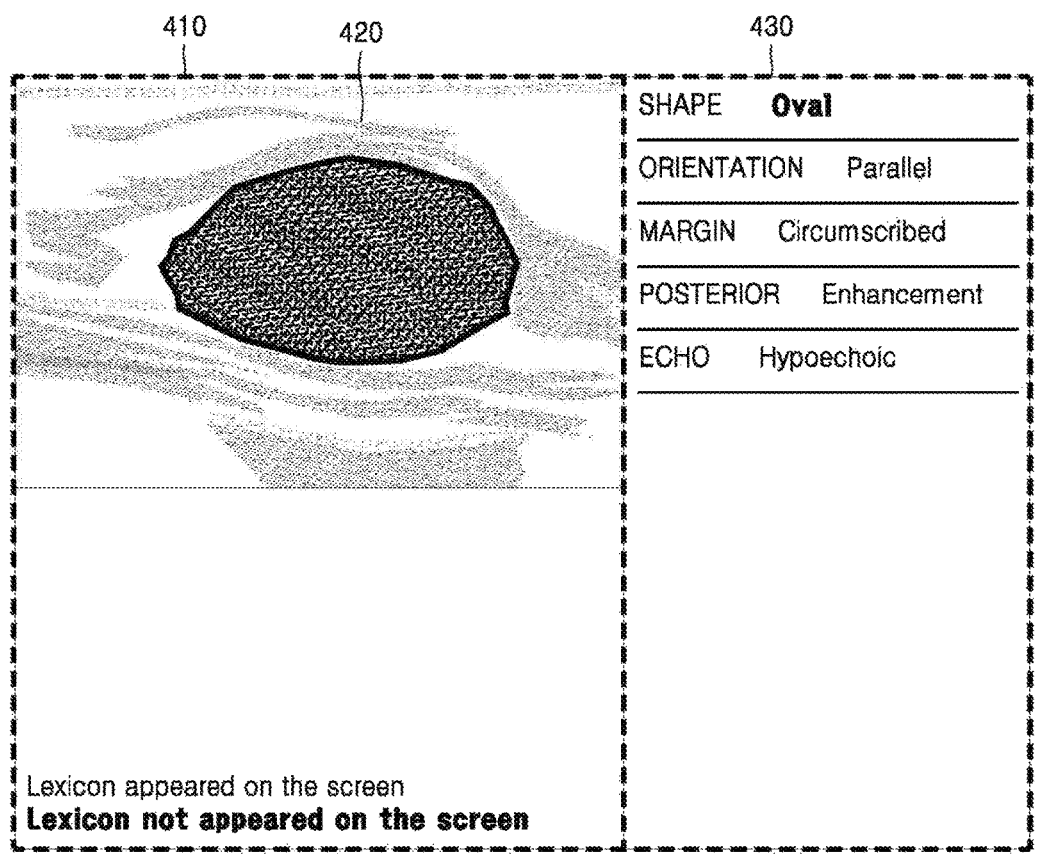
FIGS. 4 and 5 illustrate examples in which a medical imaging apparatus displays a medical image and extracted properties of an object on a display, according to an embodiment.
Figure 5:
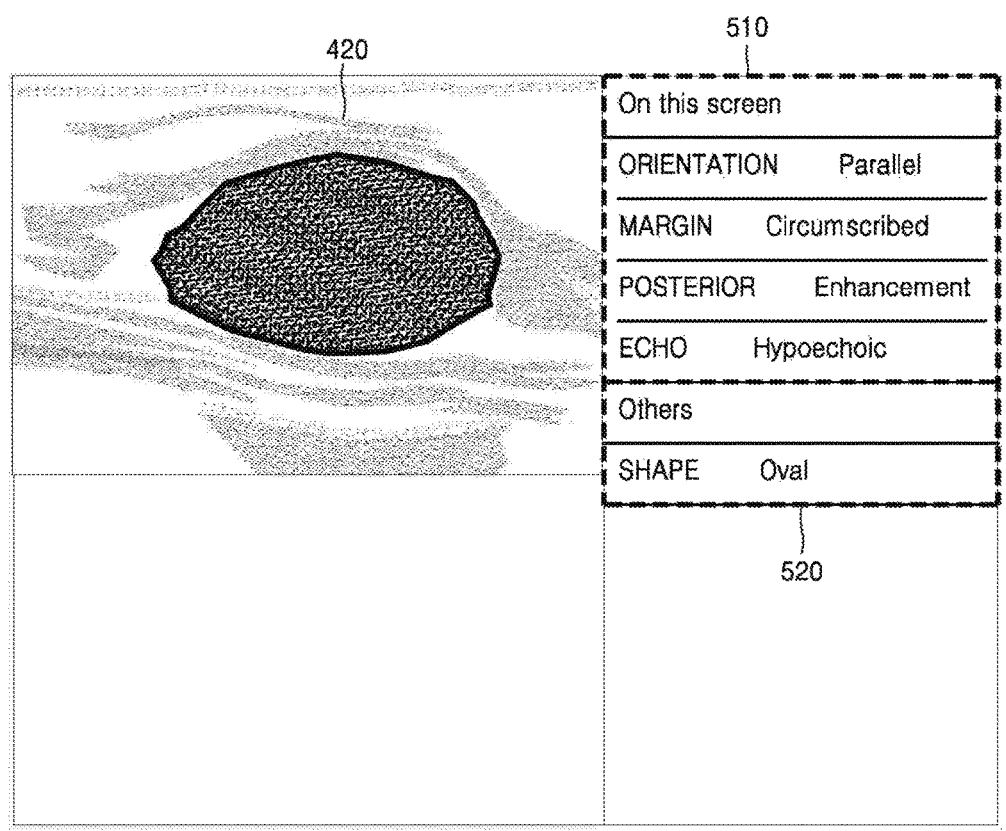

FIGS. 4 and 5 illustrate examples in which the medical imaging apparatus 100 displays a medical image and extracted properties of an object on the display 130, according to an embodiment.

Referring to FIGS. 4 and 5, the medical imaging apparatus 100 may extract properties that the object has with respect to at least one feature by using a plurality of ultrasound images. For example, as shown in FIG. 4, the medical imaging apparatus 100 may extract a property that a shape of the object is oval, a property that an orientation of the object is parallel to a surface, a margin property of the object, a property that an echo from the object is hypoechoic, etc., but embodiments are not limited thereto.

The medical imaging apparatus 100 may display, in a first region 410, a first ultrasound image 420 from among a plurality of ultrasound images generated based on ultrasound data. In this case, the first ultrasound image 420 may be a representative image that best represents extracted properties of the object from among the plurality of ultrasound images. For example, the first ultrasound image 420 may be an image showing a greatest number of properties determined as properties of the object from among the plurality of ultrasound images. The first ultrasound image 420 may be an image not showing only a property that the shape of the object is oval but showing a greatest number of extracted properties from among the plurality of ultrasound images. Alternatively, the first ultrasound image 420 may be an image selected by the user. For example, if the user presses a freeze button during ultrasound imaging, the first ultrasound image 420 may be an image obtained at a time point when the user presses the freeze button. However, embodiments are not limited thereto, and the first ultrasound image 420 may be selected using various other methods.

Furthermore, the medical imaging apparatus 100 may display, in a second region 430, properties of the object extracted based on the plurality of ultrasound images. The medical imaging apparatus 100 may display the extracted properties of the object in such a manner as to distinguish properties shown in the first ultrasound image 420 from properties not shown therein.

For example, as shown in FIG. 4, the shape of the object shown in the first ultrasound image 420 may be round, or a shape property (oval) of the object may not be shown in the first ultrasound image 420. In this case, properties (e.g., Parallel, Circumscribed, Enhancement, and Hypoechoic) shown in the first ultrasound image 420 may be displayed in a first color while properties (e. g., Oval) not shown therein may be displayed in a second color.

Furthermore, the medical imaging apparatus 100 may indicate that the properties displayed in the first color are those shown in the first ultrasound image 420 by displaying a phrase "Lexicon appeared on the screen" in the first color. The medical imaging apparatus 100 may also indicate that the properties displayed in the second color are those not shown in the first ultrasound image 420 by displaying a phrase "Lexicon not appeared on the screen" in the second color. However, embodiments are not limited thereto, and the extracted properties may be displayed in various other ways.

Alternatively, as shown in FIG. 5, the medical imaging apparatus 100 may display properties (e.g., Parallel, Circumscribed, Enhancement, and Hypoechoic) shown in a first ultrasound image 420 in a first sub-region 510 included in a second region. The imaging apparatus 100 may also display properties (e.g., Oval) not shown in the first ultrasound image 420 in a second sub-region 520 included in the second region.

In this case, a phase "On this screen" representing properties shown in the first ultrasound image 420 may be displayed in the first sub-region 510 while a phrase "Others" representing properties not shown in the first ultrasound image 420 may be displayed in the second sub-region 520. However, embodiments are not limited thereto, and the extracted properties may be displayed in various other ways.

According to an embodiment, the medical imaging apparatus 100 may display properties shown in an ultrasound image displayed on the display 130 and properties not shown therein in so that the properties may be distinguished from each other, thereby allowing a user to easily distinguish between the properties shown in the ultrasound image and those not shown therein.

Figure 6A:
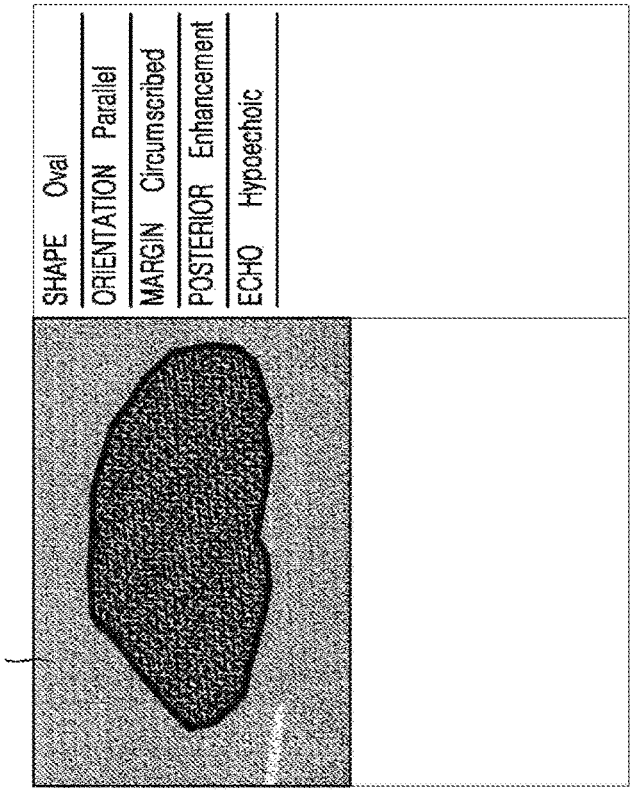
Figure 6B:
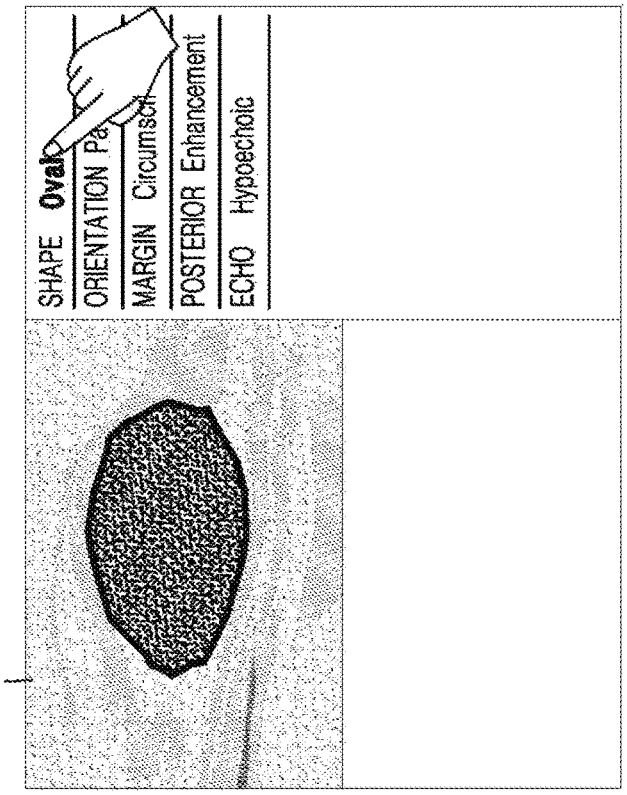

FIGS. 6A and 6B are diagrams for explaining a method, performed by the medical imaging apparatus 100, of displaying a medical image corresponding to a selected property according to an embodiment.

Referring to FIG. 6A, the medical imaging apparatus 100 may display, in a first region, a first ultrasound image 610 from among a plurality of ultrasound images generated based on ultrasound data. In this case, the first ultrasound image 610 may be a representative image that best represents extracted properties of an object from among the plurality of ultrasound images.

Furthermore, the medical imaging apparatus 100 may display properties shown in the first ultrasound image 610 from among the extracted properties of the object in a different color than properties not shown in the first ultrasound image 610, as described in detail with reference to FIGS. 4 and 5. Thus, descriptions thereof will be omitted here.

As shown in FIG. 6A, the medical imaging apparatus 100 may receive a user input for selecting a property (e.g., Oval) not shown in the first ultrasound image 610. For example, the user may touch a feature representing a property not shown in the first ultrasound image 610. However, embodiments are not limited thereto, and the user may perform an input for selecting one of the properties not shown in the first ultrasound image 610 by using various input devices.

When a property not shown in the first ultrasound image 610 is selected, as shown in FIG. 6B, the medical imaging apparatus 100 may detect and display a second ultrasound image 620 that best represents the selected property.

When the second ultrasound image 620 is displayed, the medical imaging apparatus 100 may display properties shown in the second ultrasound image 620 in a different color than properties not shown in the second ultrasound image 620.

Figure 7A:
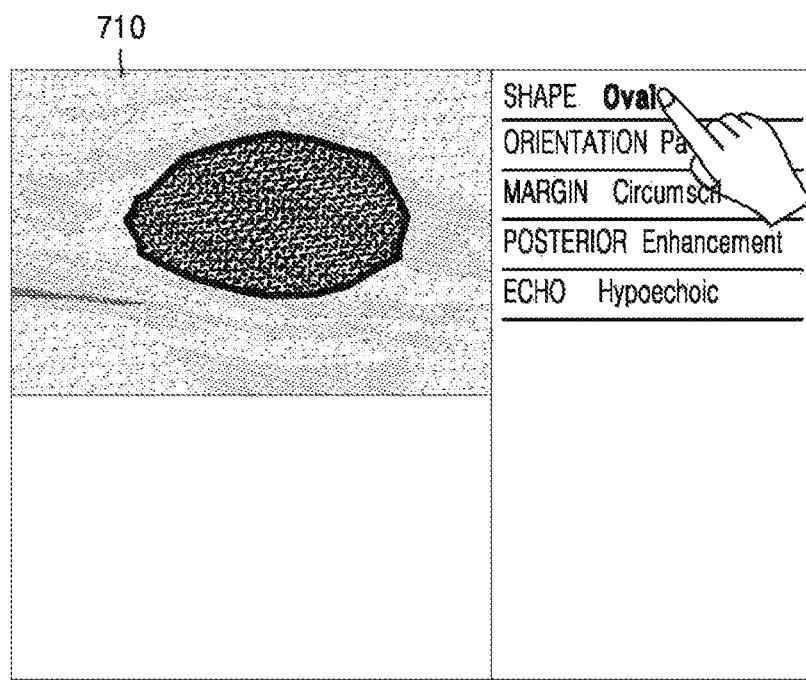
Figure 7B:
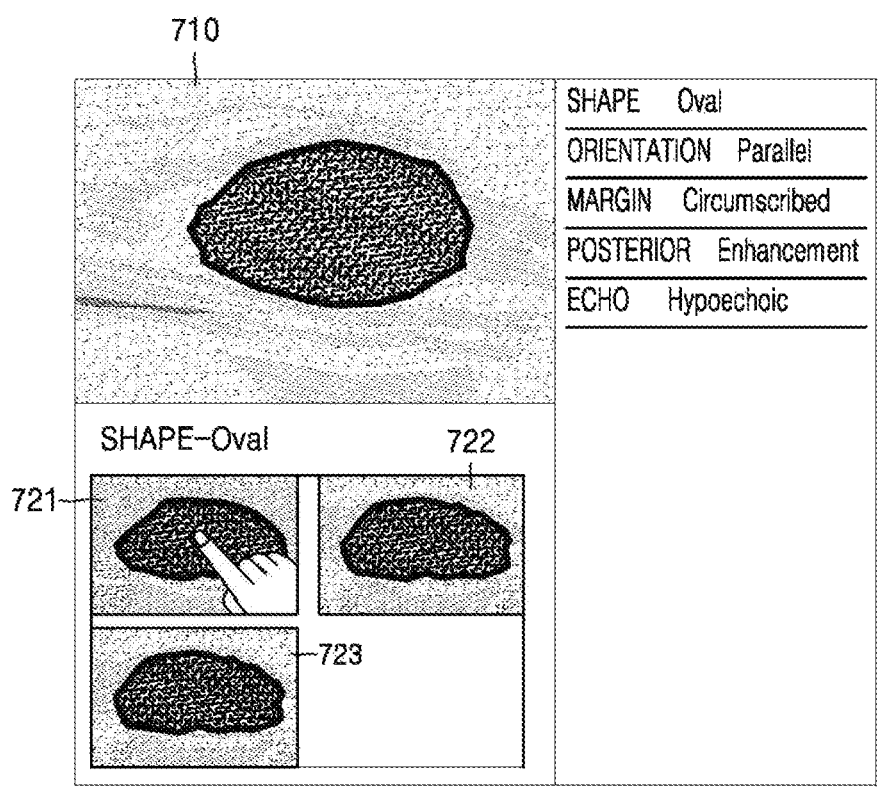
Figure 7C:
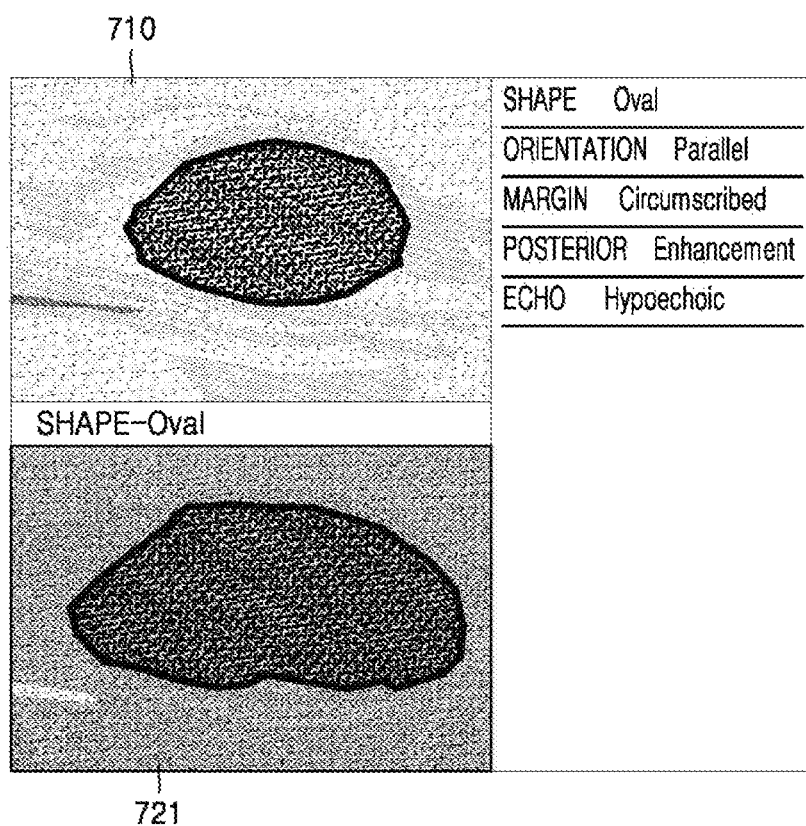

For example, when the second ultrasound image 620 is displayed, as shown in FIG. 6B, a shape property of the object (e.g., Oval) may be shown in the second ultrasound image 620, unlike in the first ultrasound image 610, and thus may be displayed in a first color that is different from a second color in which the shape property of the object not shown in the first ultrasound image 610 is displayed FIGS. 7A through 7C are diagrams for explaining a method, performed by the medical imaging apparatus 100, of displaying a medical image corresponding to a selected property according to an embodiment.

Referring to FIG. 7A, the medical imaging apparatus 100 may display may display, in a first region, a first ultrasound image 710 from among a plurality of ultrasound images generated based on ultrasound data. In this case, the first ultrasound image 710 may be a representative image that best represents extracted properties of an object from among the plurality of ultrasound images.

Furthermore, the medical imaging apparatus 100 may display properties shown in the first ultrasound image 710 from among the extracted properties of the object in a different color than properties not shown therein.

As shown in FIG. 7A, the medical imaging apparatus 100 may receive a user input for selecting a property not shown in the first ultrasound image 710. For example, the user may touch a feature representing a property not shown in the first ultrasound image 710. However, embodiments are not limited thereto, and the user may perform an input for selecting one of the properties not shown in the first ultrasound image 710 by using various input devices.

When a property not shown in the first ultrasound image 710 is selected, as shown in FIG. 7B, the medical imaging apparatus 100 may detect and display candidate images 721 through 723 showing the selected property from among the plurality of ultrasound images. The medical imaging apparatus 100 may display the candidate images 721 through 723 separately in a region distinguished from the first region where the first ultrasound image 710 is displayed. Furthermore, the medical imaging apparatus 100 may display the property (e.g., SHAPE-Oval) corresponding to the candidate images 721 through 723, together with the candidate images 721 through 723.

When the candidate images 721 through 723 are displayed, the user may select a second ultrasound image 721 that best reflects the selected property from among the candidate images 721 through 723.

Referring to FIG. 7C, when the second ultrasound image 721 is selected, the medical imaging apparatus 100 may display only the second ultrasound image while not displaying the other candidate images 722 and 723.

Figure 8B:
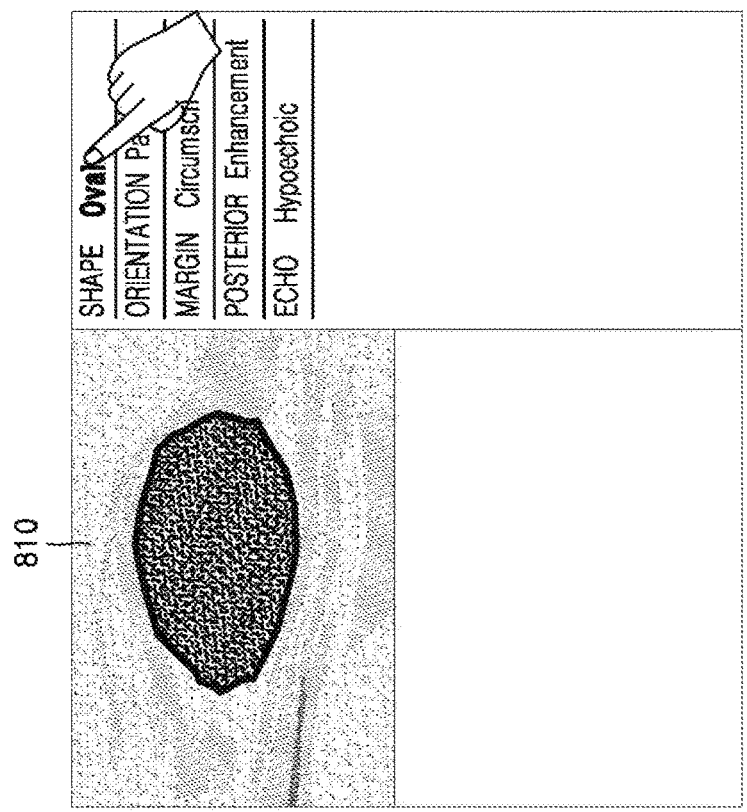
Figure 8A:
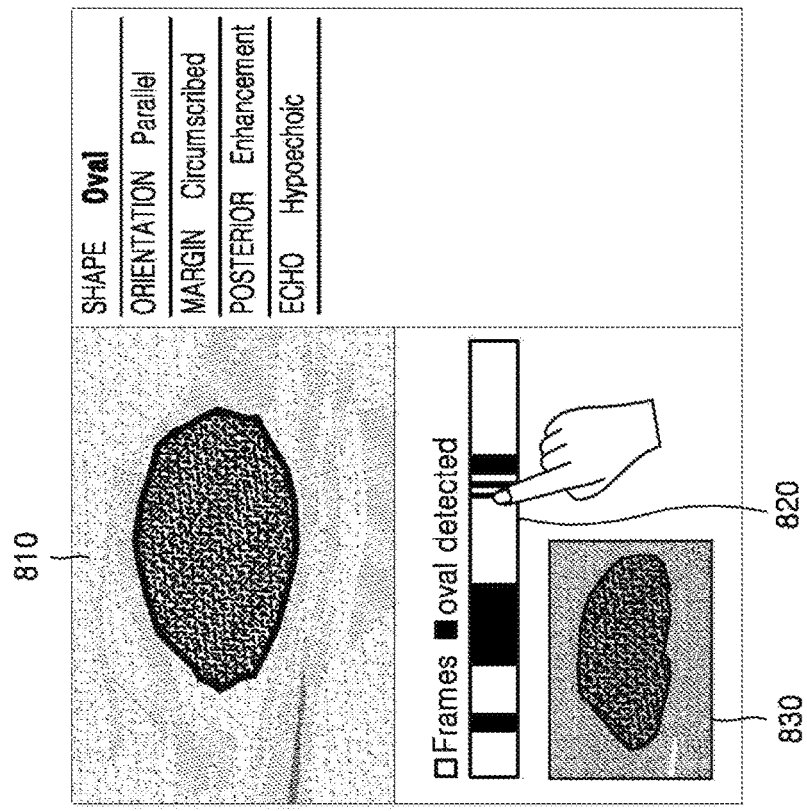

FIGS. 8A and 8B are diagrams for explaining a method, performed by the medical imaging apparatus 100, of displaying a medical image corresponding to a selected property according to an embodiment.

Referring to FIG. 8A, the medical imaging apparatus 100 may display, in a first region, a first ultrasound image 810 from among a plurality of ultrasound images generated based on ultrasound data. In this case, the first ultrasound image 810 may be a representative image that best represents extracted properties of an object from among the plurality of ultrasound images.

Furthermore, the medical imaging apparatus 100 may display properties shown in the first ultrasound image 810 from among the extracted properties of the object in a different color than properties not shown therein.

As shown in FIG. 8A, the medical imaging apparatus 100 may receive a user input for selecting a property not shown in the first ultrasound image 810. For example, the user may touch a feature representing a property not shown in the first ultrasound image 810. However, embodiments are not limited thereto, and the user may perform an input for selecting one of the properties not shown in the first ultrasound image 810 by using various input devices.

When a property not shown in the first ultrasound image 810 is selected, as shown in FIG. 8B, the medical imaging apparatus 100 may display a frame bar 820 including objects respectively representing the plurality of ultrasound images. Although FIG. 8B shows that an object is represented by a line, embodiments are not limited thereto. The object may be represented by a dot, a quadrangle, etc.

For example, if a shape property of the object (a property that a shape of the object is "oval") is selected, the medical imaging apparatus 100 may determine whether the shape of the object is shown as being "oval" in each of the plurality of ultrasound images, display a line corresponding to an ultrasound image showing the shape of the object as being oval in a first color, and display a line corresponding to an ultrasound image not showing the shape of the object as being oval in a second color.

Thus, the user may easily distinguish an ultrasound image representing the shape of the object as oval from an ultrasound image not representing the shape of as oval.

Furthermore, when one line is selected from among lines in the frame bar, the medical imaging apparatus 100 may display a second ultrasound image 830 corresponding to the selected line separately in a region distinguished from the first region where the first ultrasound image 810 is displayed. Thus, the user may easily view the second ultrasound image 830 representing the shape of the object as oval by selecting one of the lines displayed in the first color.

FIGS. 9A and 9B are diagrams for explaining a method, performed by the medical imaging apparatus 100, of displaying a medical image corresponding to a selected property according to an embodiment.

Referring to FIG. 9A, the medical imaging apparatus 100 may display, in a first region, a first ultrasound image 910 from among a plurality of ultrasound images generated based on ultrasound data. In this case, the first ultrasound image 910 may be a representative image that best reflects extracted properties of an object from among the plurality of ultrasound images.

Furthermore, the medical imaging apparatus 100 may display properties shown in the first ultrasound image 910 from among the extracted properties of the object in a different color than properties not shown therein.

As shown in FIG. 9A, the medical imaging apparatus 100 may receive a user input for selecting a property not shown in the first ultrasound image 910. For example, the user may touch a feature representing a property not shown in the first ultrasound image 910. However, embodiments are not limited thereto, and the user may perform an input for selecting one of the properties not shown in the first ultrasound image 910 by using various input devices.

When one of the properties not shown in the first ultrasound image 910 is selected, as shown in FIG. 9B, the medical imaging apparatus 100 may display a graph 920 by quantifying the degree to which the selected property is shown in each of the plurality of ultrasound images. For example, if the selected property is a shape property of the object (a property that a shape of the object is "oval"), the graph 920 may be obtained by converting into numerical values an oval degree to which the shape of the object is shown as being oval in each of the plurality of ultrasound images. In the graph 920, the abscissa and ordinate respectively denote each of the plurality of ultrasound images and a numerical value assigned to the degree to which the shape of the object is shown as being oval. In this case, the medical imaging apparatus 100 may assign a higher value as the shape of the object in an ultrasound image becomes more oval while assigning a lower value as the shape of the object in an ultrasound image becomes less oval. However, embodiments are not limited thereto.

Thus, the user may use the graph 920 to easily determine the degree to which a property of the object is shown in each of the plurality of medical images.

Furthermore, as shown in FIG. 9B, when a point on the graph 920 is selected, the medical imaging apparatus 100 may display a second ultrasound image 930 corresponding to the selected point separately in a region distinguished from the first region where the first ultrasound image 910 is displayed.

Figure 10A:
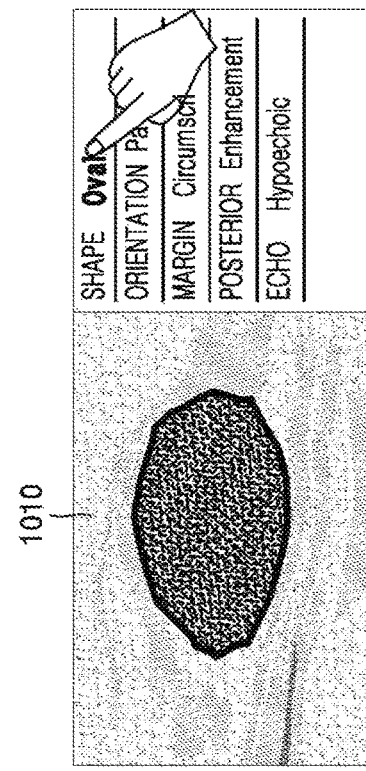
Figure 10B:
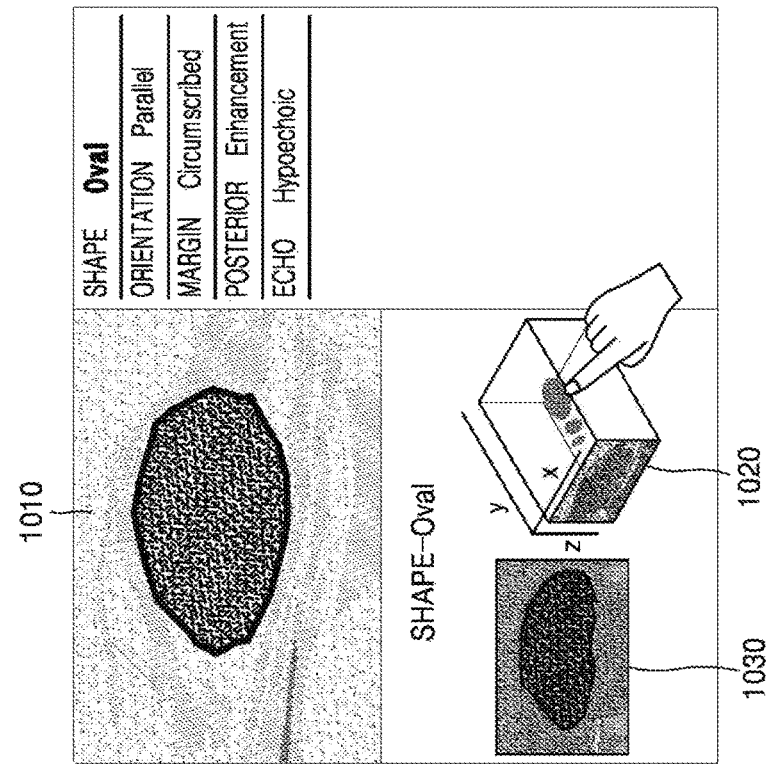

FIGS. 10A and 10B are diagrams for explaining a method, performed by the medical imaging apparatus 100, of displaying a medical image corresponding to a selected property according to an embodiment.

Referring to FIG. 10A, the medical imaging apparatus 100 may display, in a first region, a first ultrasound image 1010 from among a plurality of ultrasound images generated based on ultrasound data. In this case, the first ultrasound image 1010 may be a representative image that best reflects extracted properties of an object from among the plurality of ultrasound images.

Furthermore, the medical imaging apparatus 100 may display properties shown in the first ultrasound image 1010 from among the extracted properties of the object in a different color than properties not shown therein.

As shown in FIG. 10A, the medical imaging apparatus 100 may receive a user input for selecting a property not shown in the first ultrasound image 1010. For example, the user may touch a feature representing a property not shown in the first ultrasound image 1010. However, embodiments are not limited thereto, and the user may perform an input for selecting one of the properties not shown in the first ultrasound image 1010 by using various input devices.

When one of the properties not shown in the first ultrasound image 1010 is selected, as shown in FIG. 10B, the medical imaging apparatus 100 may display a 3D volume model 1020 corresponding to 3D volume data with respect to the object. A region exhibiting the selected property may be indicated on the 3D volume model 1020. In this case, the region exhibiting the selected property may be displayed in a color that is different from a color in which the other regions in the 3D volume model 1020 are displayed. For example, the region exhibiting the selected property may be displayed in a second color while the other regions are displayed in a first color.

Furthermore, as shown in FIG. 9B, when a point on the 3D volume model 1020 is selected, the medical imaging apparatus 100 may display a second ultrasound image 1030 corresponding to the selected point separately in a region distinguished from the first region where the first ultrasound image 1010 is displayed. In this case, the selected point may be a point included in the region displayed in the second color, and the second ultrasound image 1030 may be an ultrasound image showing the selected property.

Figure 11:
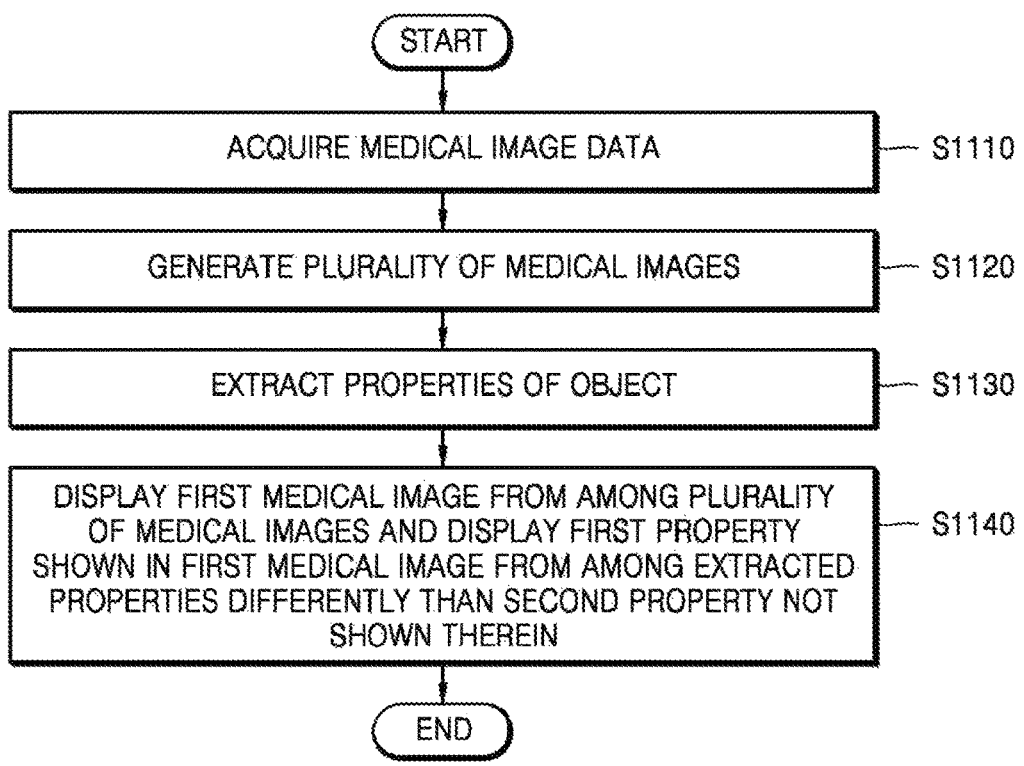
FIG. 11 is a flowchart of a method of operating a medical imaging apparatus according to an embodiment.

FIG. 11 is a flowchart of a method of operating the medical imaging apparatus 100 according to an embodiment.

Referring to FIG. 11, according to an embodiment, the medical imaging apparatus 100 may acquire medical image data (S1110).

For example, the medical image data may include ultrasound data, CT data, MR data, etc. The medical imaging apparatus 100 may acquire ultrasound data by transmitting ultrasound signals to an object and receiving echo signals reflected by the object.

The medical imaging apparatus 100 may generate a plurality of medical images based on the acquired medical image data (S1120).

For example, if the acquired medical image data is ultrasound data, the medical imaging apparatus 100 may generate an ultrasound image based on the ultrasound data. If the acquired medical data is MR data, the medical imaging apparatus 100 may generate an MR image based on the MR data. Furthermore, if the acquired medical data is CT data, the medical imaging apparatus 100 may generate a CT image based on the CT data. According to an embodiment, the plurality of medical images may be medical images respectively corresponding to various cross-sections of the object.

The medical imaging apparatus 100 may extract at least one property of the object from the plurality of medical images (S1130).

The medical imaging apparatus 100 may extract properties that the object has with respect to at least one feature based on the plurality of medical images. In this case, the at least one feature may include at least one of a shape, an orientation, a margin, a posterior, and an echo.

For example, the medical imaging apparatus 100 may extract, based on the plurality of medical images, a shape property, an orientation property, a margin property, a posterior property, an echo property of the object, etc. The medical imaging apparatus 100 may extract properties of the object by using various property extraction methods that are already known in the art.

The medical imaging apparatus 100 may display a first medical image from among the plurality of medical images and display a first property shown in the first medical image from among the extracted properties differently than a second property not shown therein (S1140).

In this case, the first medical image may be a representative image that best represents extracted properties of the object from among the plurality of medical images.

The medical imaging apparatus 100 may display the first property in a first color and the second property in a second color that is different from the first color. Furthermore, the medical imaging apparatus 100 may display the first property in a first region and the second property in a second region distinguished from the first region.

Figure 12:
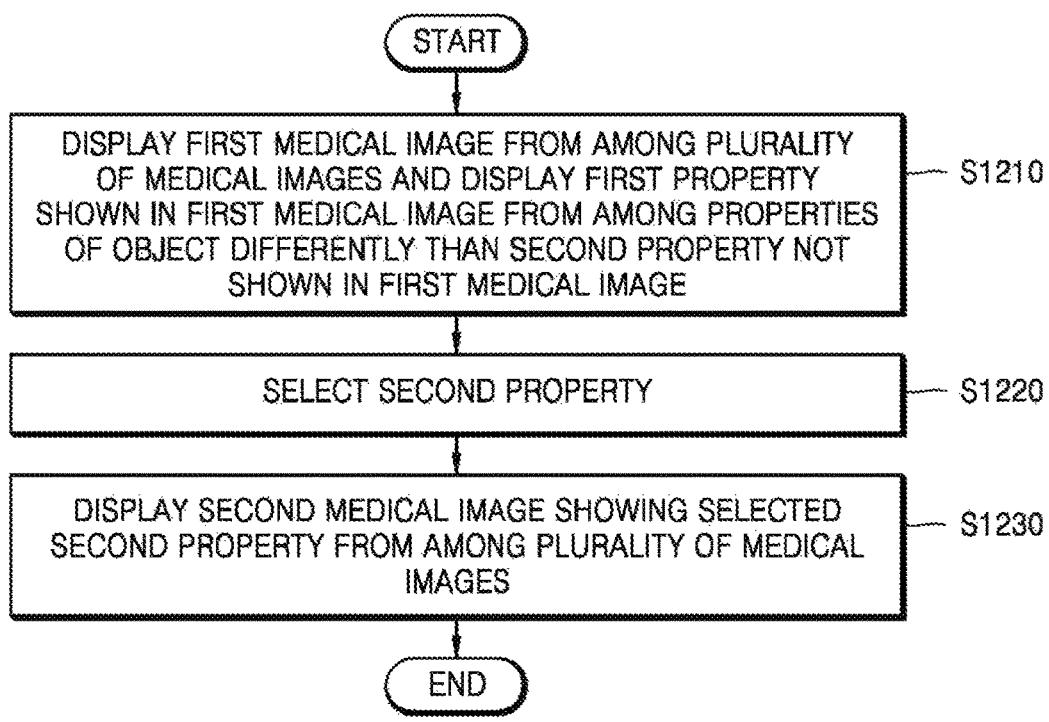
FIG. 12 is a flowchart of a method of operating a medical imaging apparatus according to an embodiment.

FIG. 12 is a flowchart of a method of operating the medical imaging apparatus 100 according to an embodiment.

Referring to FIG. 12, according to an embodiment, the medical imaging apparatus 100 may display a first medical image from among a plurality of medical images and display a first property shown in the first medical image from among extracted properties of an object differently than a second property not shown in the first medical image (S1210).

Since operation S1210 corresponds to operation S1140 described with reference to FIG. 11, a detailed description thereof will be omitted below.

The medical imaging apparatus 100 may receive a user input for selecting the second property not shown in the first medical image (S1220).

For example, the user may touch a feature representing a property not shown in the first ultrasound image. However, embodiments are not limited thereto, and the user may perform an input for selecting one of the properties not shown in the first ultrasound image by using various input devices.

The medical imaging apparatus 100 may display a second medical image showing the selected second property from among the plurality of medical images (S1230).

For example, the medical imaging apparatus 100 may automatically detect and display a medical image showing the second property from among the plurality of medical images.

The ultrasound diagnosis apparatuses and methods of operating the same according to the embodiments may be embodied as a computer-readable code on a computer-readable storage medium. The computer-readable storage medium is any data storage device that can store data which can be thereafter read by a processor. Examples of computer-readable storage media include read-only memory (ROM), random-access memory (RAM), CD-ROMs, magnetic tapes, floppy disks, optical data storage devices, etc. The computer-readable storage media can also be distributed over network coupled computer systems so that computer-readable codes are stored and executed in a distributed fashion.

While one or more embodiments have been described with reference to the figures, it will be understood by one of ordinary skill in the art that various changes in form and details may be made therein without departing from the spirit and scope of the present inventive concept as defined by the following claims. That is, all changes and modifications within the scope of the appended claims and their equivalents will be construed as being included in the present inventive concept.

What is claimed is:

1. A medical imaging apparatus comprising:
an image processor configured to extract properties that an object has with respect to at least one feature, from each medical image among a plurality of medical images of the object, by using values of pixels and a detected edge in each medical image based on at least one of pre-stored reference values and a pre-stored data, wherein the at least one feature comprises at least one of a shape, an orientation, a margin, a posterior, and an echo;
a controller configured to control a display to display a first medical image from among the plurality of medical images and the extracted properties, and display a plurality of first properties shown in the first medical image from among the properties, and a plurality of second properties from among the properties not shown in the first medical image, in such a manner that the first properties and the second properties are distinguished from each other; and
an input device configured to receive an input for selecting at least one of the second properties,
wherein the controller is further configured to:
control the display to display a list of the plurality of the first properties in a first region and display a list of the plurality of the second properties in a second region that is distinguished from the first region, and
control the display to display a second medical image showing the selected second property from among the plurality of medical images,
wherein the controller is further configured to quantify a degree to which the second property is shown in each of the plurality of medical images, and control the display to display a graph based on each quantified degree.

2. The medical imaging apparatus of claim 1, further comprising a receiver configured to acquire ultrasound data with respect to the object,
wherein the image processor is further configured to generate a plurality of ultrasound images based on the ultrasound data, and extract the properties that the object has with respect to the at least one feature, based on the plurality of ultrasound images.

3. The medical imaging apparatus of claim 1, wherein the controller is further configured to control the display to display the first property in a first color and display the second property in a second color that is different from the first color.

4. The medical imaging apparatus of claim 1,
wherein the controller is further configured to control the display to display a frame bar including lines respectively corresponding to the plurality of medical images and to display a line corresponding to a medical image showing the selected second property from among the lines and a line corresponding to a medical image not showing the second property in such a manner that the lines are distinguished from each other.

5. The medical imaging apparatus of claim 4, wherein the input device is further configured to receive an input for selecting one of the lines in the frame bar, and
wherein the controller is further configured to control the display to display a medical image corresponding to the selected line.

6. The medical imaging apparatus of claim 1, wherein the input device is further configured to receive an input for selecting a point on the graph, and wherein the controller is further configured to control the display to display a medical image corresponding to the selected point.

7. A method of operating a medical imaging apparatus, the method comprising:
  extracting properties that an object has with respect to at least one feature from each medical image among a plurality of medical images of the object, by using values of pixels and a detected edge in each medical image based on at least one of pre-stored reference values and a pre-stored data, wherein the at least one feature comprises at least one of a shape, an orientation, a margin, a posterior, and an echo;
  displaying a first medical image from among the plurality of medical images, and the extracted properties;
  displaying a plurality of first properties shown in the first medical image from among the properties, and a plurality of second properties from among the properties not shown in the first medical image, in such a manner that the first properties and the second properties are distinguished from each other;
  wherein the displaying of the plurality of first properties and the plurality of second properties comprises displaying the plurality of first properties in a first region and displaying the plurality of second properties in a second region that is distinguished from the first region, and
  receiving an input, via an input device, indicating a selection of at least one of the second properties;
  displaying a second medical image showing the selected second property from among the plurality of medical images; and
  quantifying a degree to which the second property is shown in each of the plurality of medical images, and displaying a graph based on each quantified degree.

8. The method of claim 7, further comprising acquiring ultrasound data with respect to the object,
  wherein the extracting of the properties comprises:
  generating a plurality of ultrasound images based on the ultrasound data; and
  extracting the properties that the object has with respect to the at least one feature based on the plurality of ultrasound images.

9. The method of claim 7, wherein the displaying of the first property and the second property in such a manner that the first property and the second property are distinguished from each other comprises displaying the first property in a first color and displaying the second property in a second color that is different from the first color.

10. The method of claim 7, further comprising:
  displaying a frame bar including lines respectively corresponding to the plurality of medical images and displaying a line corresponding to a medical image showing the selected second property from among the lines and a line corresponding to a medical image not showing the second property in such a manner that the lines are distinguished from each other.

11. The method of claim 10, further comprising:
  receiving an input for selecting one of the lines in the frame bar; and
  displaying a medical image corresponding to the selected line.

12. The method of claim 7, further comprising:
  receiving an input for selecting a point on the graph; and
  displaying a medical image corresponding to the selected point.

13. A medical imaging apparatus comprising:
  an image processor configured to extract properties that an object has with respect to at least one feature, from each medical image among a plurality of medical images of the object, by using values of pixels and a detected edge in each medical image based on at least one of pre-stored reference values and a pre-stored data, wherein the at least one feature comprises at least one of a shape, an orientation, a margin, a posterior, and an echo;
  a controller configured to:
    determine a number of properties present in each medical image of the plurality of medical images,
    control a display to display a first medical image that shows a greatest number of types of properties from among the plurality of medical images, and the extracted properties,
    control the display to display a plurality of first properties shown in the first medical image from among the properties, and a plurality of second properties from among the properties not shown in the first medical image, in such a manner that the first properties and the second properties are distinguished from each other; and
  an input device configured to receive an input for selecting at least one of the second properties,
  wherein the controller is further configured to:
    control the display to display a list of the plurality of the first properties in a first region, and display a list of the plurality of the second properties in a second region that is distinguished from the first region, and
    control the display to display a second medical image showing the selected second property from among the plurality of medical images.

14. A method of operating a medical imaging apparatus, the method comprising:
  extracting properties that an object has with respect to at least one feature from each medical image among a plurality of medical images of the object, by using values of pixels and a detected edge in each medical image based on at least one of pre-stored reference values and a pre-stored data, wherein the at least one feature comprises at least one of a shape, an orientation, a margin, a posterior, and an echo;
  determining a number of properties present in each medical image of the plurality of medical images;
  displaying a first medical image that shows a greatest number of types of properties from among the plurality of medical images, and the extracted properties;
  displaying a plurality of first properties shown in the first medical image from among the properties, and a plurality of second properties from among the properties not shown in the first medical image, in such a manner that the first properties and the second properties are distinguished from each other;
  wherein the displaying of the plurality of first properties and the plurality of second properties comprises displaying the plurality of first properties in a first region and displaying the plurality of second properties in a second region that is distinguished from the first region, and
  receiving an input, via an input device, indicating a selection of at least one of the second properties; and
  displaying a second medical image showing the selected second property from among the plurality of medical images.

* * * * *